US00PP14827P3

(12) United States Plant Patent
Hasegawa

(10) Patent No.: US PP14,827 P3
(45) Date of Patent: May 25, 2004

(54) HYBRID CARNATION PLANT NAMED 'CFPC CHARM'

(50) Latin Name: *Dianthus caryophyllus*
Varietal Denomination: CFPC Charm

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,170

(22) Filed: Jul. 29, 2002

(65) Prior Publication Data

US 2004/0019945 P1 Jan. 29, 2004

(51) Int. Cl.[7] ..... A01H 5/00
(52) U.S. Cl. ..... Plt./278
(58) Field of Search ..... Plt./278

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive dark hot pink flowers.

1 Drawing Sheet

Classification: The present invention relates to a new Hybrid *Dianthus caryophyllus* plant.

Variety denomination: The new plant has the varietal denomination 'CFPC Charm'.

BACKGROUND OF THE INVENTION

The present invention relates to a new and distinct variety of carnation plant which was originated by me by crossing two undistributed unpatented seedlings identified as '970152' (female parent) and '970161' (male parent). The varietal denomination of the new variety is 'CFPC Charm'.

SUMMARY OF THE INVENTION

Among the novel characteristics possessed by the new variety which distinguish it from other varieties of which I am aware, are its unusual dark hot pink flowers which retain color without fading. When grown in a greenhouse in Salinas, Calif., in 4½ inch plastic pots, pinched plants are about 9½ inches tall and about 7 inches in diameter. Flower diameter averages about 2 inches with a crown of about 1 inch (average). Foliage is about 3⅝ inches long and about ⅜ inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENTS

The new variety differs from its parents in flower color. The female parent produces salmon pink flowers, and the male parent produces red flowers.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, type, suitable for cut flower production and as a pot spray.

Plant:
- *Height.*—About 9½ inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Very vigorous and free-breaking plant habit with strong straight stems.
- *Mutation prone.*—No.
- *Disease resistance.*—Good, resistence to soil-borne diseases such as *Fusarium oxysporum,* and *F. graminearum* and root-rots such as damping off, water molds and the like as is typical of carnations.
- *Temperature tolerance.*—Wide range.

Foliage (base of plant):
- *Color.*—Upper side: Near 137A, occasional radial color breaks of near 66C on upper side of petals. Lower side: Near 137B.
- *Size.*—About 3⅝ inches long and about ⅜ inch wide.
- *Leaf base and apex.*—Leaf base edge smooth, color near 138C; leaf apex edge smooth, color near 137A.
- *Quantity.*—Numerous.

*Shape.*—Lanceolate.
*Texture.*—Smooth.
*Ribs.*—Central keel.
*Arrangement.*—Bi-lateral along stem.
*Stem.*—Color: Near 137A. Size: Stem diameter of about ¼ inch.
*Bud.*—Shape: Ovoid. Color: Near 144A. Length: About 1⅛ inches. Diameter: About ⅞ inch.
*Calyx.*—Sepals: About 5. Length: About 5/16 inch. Width: About 5/16 inch. Color Outside: Near 144A. Inside: Near 145C.

Bloom:
*Shape.*—Rounded.
*Size.*—Diameter: About 2 inches. Depth: About 1 inch.
*Borne.*—As a spray.
*Color.*—General tonality: Red purple group. Upper side: Near 57C. Lower side: Near 66C. Center: Near 57C. Outer petals: Near 57C.
*Permanence.*—Dry up on receptacle.
*Keeping quality.*—Very good.
*Fragrance.*—Fragrant.

Petalage:
*Quantity.*—About 21.
*Outer petal size.*—Length: About 1 15/16 inches. Width: About 1⅜ inches.
*Central petal size.*—Length: About 1¾ inches. Width: About 1⅛ inches.
*Texture.*—Smooth.
*Appearance.*—Shiny, petal edge smooth with occasional coarse serrations, color upper side near 57C, color lower side 66C.
*Form.*—Fan shaped.

Reproductive organs:
*Stamen.*—None.
*Anthers.*—None.
*Filaments.*—None.
*Pistil.*—1. Length: About 1 5/16 inches. Color: Whiter than 155D.
*Stigma.*—2. Color: Near 58D.
*Fertility.*—Male: Sterile. Female: Good.
*Ovary.*—Shape: Conical. Color Base: Near 155D. Body: Near 144A. Apex: Near 144A.
*Fruit.*—No fruit or seed produced.

I claim:

1. A new and distinct carnation plant of the variety substantially as herein shown and described.

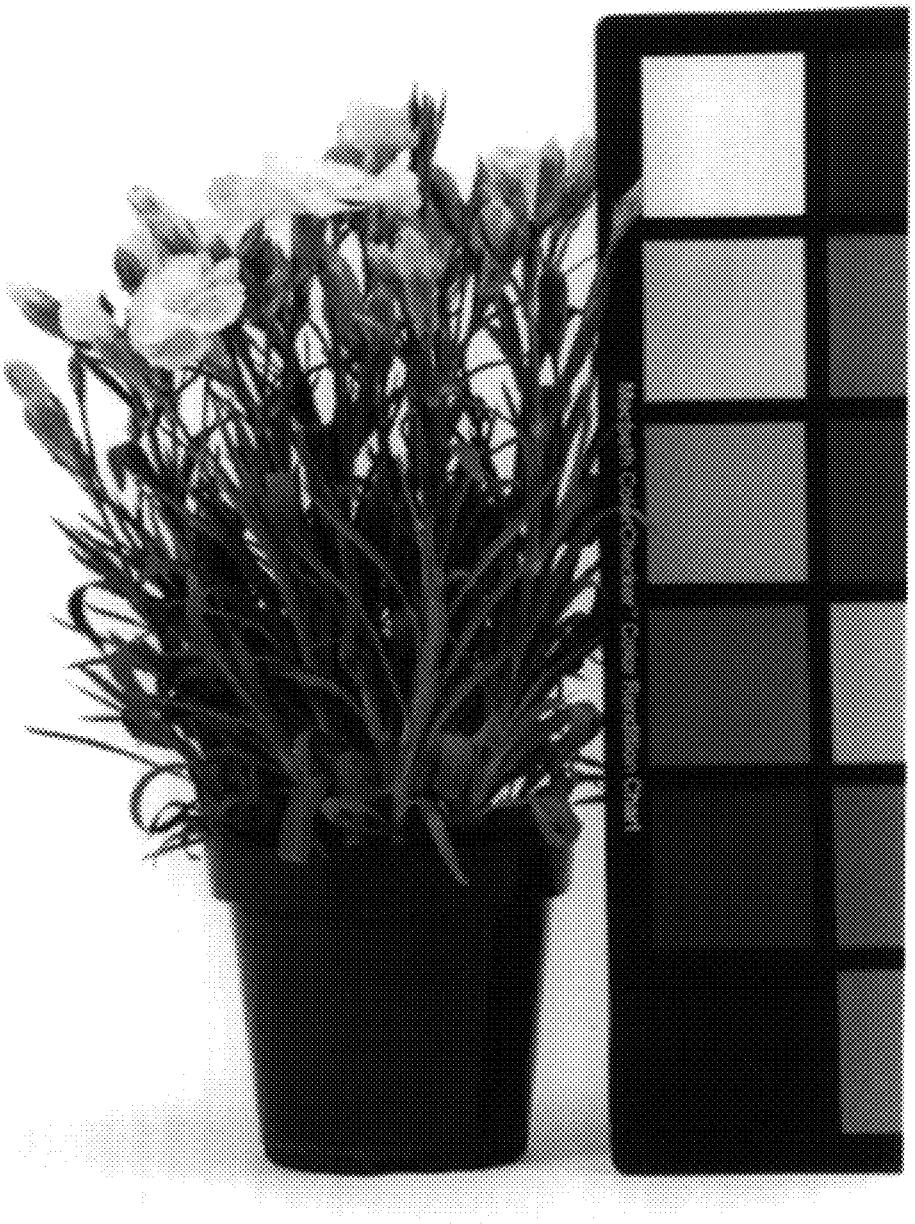

* * * * *